(12) United States Patent
Tulkki et al.

(10) Patent No.: US 6,672,172 B2
(45) Date of Patent: Jan. 6, 2004

(54) TRIGGERED FLOW MEASUREMENT

(75) Inventors: Sauli Tulkki, Uppsala (SE); Leif Smith, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 166 days.

(21) Appl. No.: 09/771,703

(22) Filed: Jan. 30, 2001

(65) Prior Publication Data

US 2002/0043113 A1 Apr. 18, 2002

Related U.S. Application Data

(60) Provisional application No. 60/179,136, filed on Jan. 31, 2000.

(51) Int. Cl.[7] .................................................. G01P 5/18
(52) U.S. Cl. .................................. 73/861.05; 73/861.95
(58) Field of Search ..................... 73/861.95, 861.05; 600/504, 505, 481, 549, 506

(56) References Cited

U.S. PATENT DOCUMENTS

| | | | |
|---|---|---|---|
| 5,226,333 A | * 7/1993 | Hess | 166/241.5 |
| 5,526,817 A | 6/1996 | Pfeiffer et al. | 128/691 |
| 5,595,181 A | 1/1997 | Hubbard | 128/692 |
| 6,089,103 A | * 7/2000 | Smith | 600/486 |
| 6,325,762 B1 | * 12/2001 | Tjin | 356/336 |
| 6,387,052 B1 | * 5/2002 | Quinn et al. | 600/505 |
| 6,394,961 B1 | * 5/2002 | Pfeiffer et al. | 600/505 |

FOREIGN PATENT DOCUMENTS

| | | | |
|---|---|---|---|
| DE | 0 900 545 A2 | * 5/2002 | ........... A61B/5/028 |
| EP | 0 900 545 | 3/1999 | |
| WO | WO 93/21823 | 11/1993 | |

OTHER PUBLICATIONS

Ganz et al., "Measurement of Coronary Sinus Blood Flow by Continuous Thermodilution in Man," Circulation, vol. XLIV, No. 2, Aug. 1971, pp. 181–195.

* cited by examiner

*Primary Examiner*—Edward Lefkowitz
*Assistant Examiner*—Corey D. Mack
(74) *Attorney, Agent, or Firm*—Foley & Lardner

(57) ABSTRACT

When a bolus dose of cold saline is injected into a catheter where a wire, carrying a sensor unit and electrical leads for signal transmission, is located, the lead resistance is affected by the cold saline thereby altering the resistivity. However, by countering this effect and measuring the change needed to affect this countermeasure, a resistance variation curve can be generated. An accurate starting point for the determination of a transit time can be derived from the curve. Using conventional flow measurement calculations with the accurate starting point yields a better understanding of the flow profile in an artery based on the transit time.

17 Claims, 8 Drawing Sheets

Cable signal (T)

Sensor signal (T)

TRIGGERED FLOW MEASUREMENT

The benefit of U.S. Provisional Application Serial No. 60/179,136, filed Jan. 31, 2000, claimed and the entire contents of the Provisional Application is incorporated herein by reference.

The present invention relates to measurement of flow in blood vessel by thermo-dilution. In particular it relates to an improved method of triggering such measurement in order to improve the measurements.

BACKGROUND OF THE INVENTION

Devices and methods of flow measurements are disclosed in U.S. Ser. Nos. 09/073,061, 09/117,416, all assigned to Radi Medical Systems AB, Sweden.

In particular Ser. No. 09/073,061 relates to a method of flow measurements by thermo-dilution, wherein the time measurements are triggered by a pressure pulse detected as a result of the injection of a bolus dose of saline. The general theory described therein fully applies to the present invention, and therefore the entire disclosure thereof is incorporated herein.

Nevertheless, the discussion therein is repeated below for ease of understanding.

Application of the thermodilution principle in the coronary sinus was introduced by Ganz (Ganz et al, "Measurement of coronary sinus blood flow by continuous thermodilution in man, *Circulation* 44:181–195, 1971). A small catheter is introduced deeply into the coronary sinus and cold saline is delivered at its tip. Theoretically, flow can be calculated from the changes in blood temperature, registered by a thermistor close to the outlet of the coronary sinus. An advantage of this method is that only right heart catheterization is required.

The principle of thermo-dilution involves injecting a known amount of cooled liquid, e.g. physiological saline in a blood vessel. After injection the temperature is continuously recorded with a temperature sensor attached to the tip of a guide wire that is inserted in the vessel. A temperature change due to the cold liquid passing the measurement site, i.e. the location of the sensor, will be a function of the flow.

There are various methods of evaluating the temperature signal for diagnostic purposes. Either one may attempt to calculate the volume flow, or one may use a relative measure, where the flow in a "rest condition" is compared with a "work condition", induced by medicaments.

The latter is the simpler way, and may be carried out by measuring the width at half height of the temperature change profile in the two situations indicated, and forming a ratio between these quantities.

Another way of obtaining a ratio would be to measure the transit time from injection and until the cold liquid passes the sensor, in rest condition and in work condition respectively.

The former method, i.e. the utilization of the volume flow parameter as such, requires integration of the temperature profile over time in accordance with the equations given below $$(1) \; Q_{rest} = V \Big/ \int_{t_0}^{t_1} (T_{r,m}/T_{r,l}) dt \propto V \Big/ \int_{t_0}^{t_1} (T_{r,0} - T_{r,m}) dt \quad (3.1)$$

$$(2) \; Q_{work} = V \Big/ \int_{t_0}^{t_1} (T_{w,m}/T_{w,l}) dt \propto V \Big/ \int_{t_0}^{t_1} (T_{w,0} - T_{w,m}) dt \quad (3.2)$$

wherein
V is the volume of injected liquid
$T_{r,m}$ is the measured temperature at rest condition
$T_{r,1}$ is the temperature of injected liquid at rest condition
$T_0$ is the temperature of the blood, i.e. 37° C.
$T_{w,m}$ is the measured temperature at work condition
$T_{w,1}$ is the temperature of injected liquid at work condition
Q is the volume flow These quantities may then be used directly for assessment of the condition of the coronary vessels and the myocardium of the patient, or they may be ratioed as previously discussed to obtain a CFR, i.e. CFR=$Q_{work}/Q_{rest}$.

The latter method, i.e. determination of the transit time requires an accurate time measurement, in view of the relatively small distances in question, about 10 cm or less from injection to measurement site.

To obtain a correct measurement, the time has to be measured with some accuracy. Using a simple stop watch, which is a common means of timing, is far too inaccurate for obtaining reliable transit times.

The flow F may be obtained as follows, which is a derivation for a similar technique, namely the indicator dilution technique. This is based on a rapidly injected amount of some kind of indicator, the concentration of which is measured.

Suppose that the flow through a branching vascular bed is constant and equals F, and that a certain well-known amount M of indicator is injected into this bed at site A (see FIG. 7). After some time, the first particles of indicator will arrive at the measuring site B. The concentration of indicator at B, called c(t), will increase for some time, reach a peak and decrease again. The graphic representation of indicator concentration as a function of time is called the indicator dilution curve.

Consider M as a large number of indicator particles (or molecules). The number of particles passing at B during the time interval Δt, between $t_i$ and $t_{i+1}$, equals the number of particles per unit time multiplied by the length of the time interval, in other words: $c(t_i) \cdot F \cdot \Delta t$ (FIG. 8).

Because all particles pass at B between t=0 and t=∞, this means that:

$$M = \lim_{\Delta t \to 0} \sum_{i=0}^{\infty} (c(t_i) \cdot F \cdot \Delta t) \; \text{or} \quad (3.3)$$

$$M = \int_0^{\infty} c(t) \cdot F \cdot dt \; \text{or}$$

$$F = \frac{M}{\int_0^{\infty} c(t) \cdot dt}$$

and it is the last expression which is used in most methods to calculate systemic flow as outlined above. Essential features of this approach is that the amount M of injected indicator should be known whereas no knowledge about the volume of the vascular compartment is needed.

The calculation of volume is more complex. For this purpose, the function h(t) is introduced which is the fraction of indicator, passing per unit of time at a measurement site at time t. In other words, h(t) is the distribution function of transit times of the indicator particles. If it is assumed that the flow of the indicator is representative for flow of the total fluid (complete mixing), h(t) is also the distribution function of transit times of all fluid particles. Suppose the total volume of fluid is made up of a very large number of volume elements $dV_i$ which are defined in such a way that $dV_i$ contains all fluid particles present in the system at t=0, with transit times between $t_i$ and $t_{i+1}$. The fraction of fluid particles requiring times between $t_i$ and $t_{i+1}$ to pass the measurement site, is $h(t_i) \cdot \Delta t$ by definition. Because the rate at which the fluid particles pass at the measurement site, equals F, the rate at which the particles making up $dV_i$ pass at the measurement site is $F \cdot h(t_i) \cdot \Delta t$. The total volume of $dV_i$ equals the time $t_i$ required for all particles segments in $dV_i$ to pass at the measurement site multiplied by the rate at which they leave. In other words:

$$dV_i = t_i \cdot F \cdot h(t_i) \cdot \Delta t \quad (3.4)$$

and by integration:

$$V = F \int_0^\infty t \cdot h(t) dt \quad (3.5)$$

The integral in the equation above represents the mean transit time $T_{mn}$, which is the average time needed by one particle to travel from an injection site to a measurement site. Therefore:

$$V = F \cdot T_{mn} \quad (3.6)$$

or:

$$F = V/T_{mn}; \quad T_{mn} = V/F \quad (3.7)$$

which states the fundamental fact that flow equals volume divided by mean transit time.

The mean transit time ($T_{mn}$) can now be calculated easily from the indicator or thermo dilution curve in the following way. When looking at the hatched rectangle in FIG. 8, it can be seen that the number of indicator particles passing between $t_i$ and $t_{i+1}$, equals the number of particles $c(t_i) \cdot F$ passing per unit of time, multiplied by the length of the time interval, $\Delta t$, in other words: $c(t_i) \cdot F \cdot \Delta t$. Therefore, the total (summed) transit time of all these indicator particles together equals $t_i \cdot c(t_i) \cdot F \cdot \Delta t$. The total transit time of all indicator particles together, by integration, is $$\int_0^\infty t \cdot c(t) \cdot F \cdot dt \quad (3.8)$$

and the mean transit time of the indicator particles can be obtained by dividing equation 3.8 by the total number of particles M, resulting in:

$$T_{mn} = \frac{\int_0^\infty t \cdot c(t) \cdot F \cdot dt}{M} \quad \text{or} \quad (3.9)$$

$$T_{mn} = \frac{F}{M} \int_0^\infty t \cdot c(t) \cdot dt \quad (3.10)$$

By substitution of equation 3.3 in 3.10, $T_{mn}$ is obtained:

$$T_{mn} = \frac{\int_0^\infty t \cdot c(t) \cdot dt}{\int_0^\infty c(t) \cdot dt} \quad (3.11)$$

Equation 3.11 describes how mean transit time $T_{mn}$ can be calculated from the indicator dilution curve c(t). In the assessment of myocardial in which the contrast agent is used as the indicator, because the amount of injected contrast agent is unknown and changing (because of the necessary leakage of the contrast agent into the aorta and the unknown and changing distribution of contrast agent over the different branches of the coronary arterial tree), use of $T_{mn}$ is advantageous because no knowledge about the amount of injected indicator is necessary.

Although the above derivation was made for the mentioned indicator dilution technique, the result is the same for thermo-dilution since the same distribution function may be employed, and the skilled man will easily adjust the equations accordingly.

The prior art pressure pulse triggering of the time measurements, although improving the method considerably, has some drawbacks. For example, the sensitivity in the pressure measurement may not be adequate due to the magnitude of the pulse being quite low; therefore, the accuracy may be negatively influenced.

SUMMARY OF THE INVENTION

Thus, there is a need for an improved triggering of the measurement.

The inventors have realized that a previous problem acknowledged in connection with thermo-dilution can be used to an advantage for triggering purposes. Namely, when a bolus cold saline is injected into a catheter where a wire carrying the sensor unit and electrical leads for signal transmission is located, the lead resistance will be instantly affected by the cold saline by a change in the resistivity. This is a problem, however, because the change must be countered in order to arrive at a correct output signal.

This compensation can be done, and is one of the issues discussed in our pending Swedish application 9901962-2, corresponding to U.S. provisional No. 60/136,401.

Thus, in accordance with the present invention, the resistivity change is recorded as a resistance variation curve. Various parts of the recorded curve, or the entire curve, can be mathematically processed to yield a starting point for the determination for a transit time of the injected liquid. In this way, the accuracy in the time measurement is significantly improved.

So long as detectable signals are obtained, the method of flow determination according to the invention is advantageous in that it is independent of: (a) the injected amount of bolus liquid and (b) the temperature of the injected liquid.

DETAILED DESCRIPTION OF THE INVENTION

Figure 1:
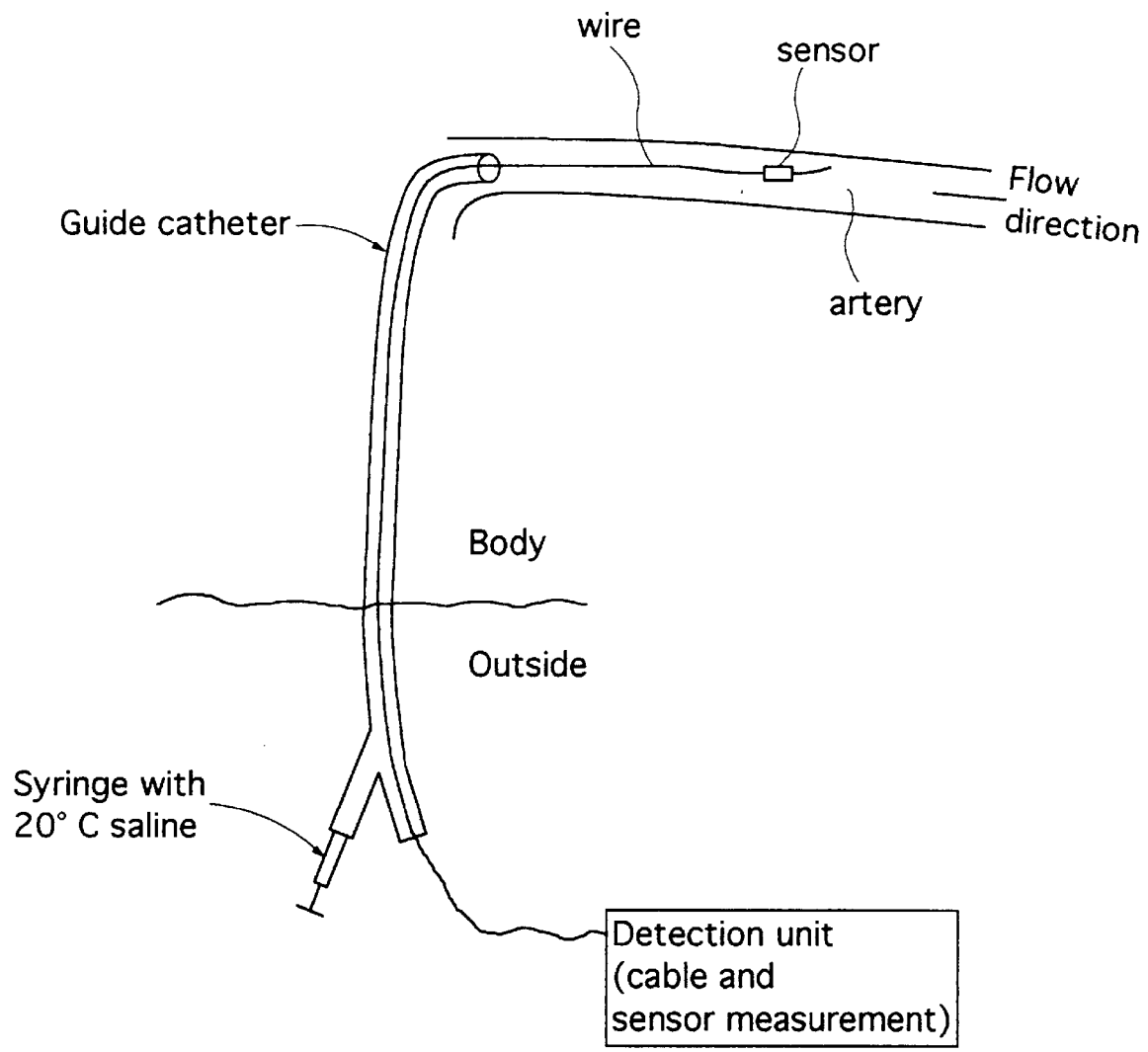
FIG. 1 is an overview that shows a system wherein the novel method is performed.

In FIG. 1 there is disclosed a system suitable for implementation of the present invention. The system comprises a hollow guide catheter insertable into the body of a patient. The distal end of the catheter functions as an outlet for liquid to be passed therethrough. The catheter is located at a point in the artery system where it is desired to know the flow. Inside the catheter a wire is inserted, the distal end of which carries a sensor unit having a temperature sensor and optionally a pressure sensor. Other additional sensors are also conceivable, e.g. pH sensors, ion selective sensors etc. The wire is extended past the distal end of the catheter such that the sensor unit is located at a relatively small distance, e.g. 10 cm, from the catheter outlet.

Alternatively, the wire can be inserted as above and positioned in an appropriate position, and then a second catheter can be passed over the wire, inside the guide catheter; the distal end of this second catheter can be positioned in the artery system where it is desired to know the flow. The first catheter will thereby only be used for guiding. This alternative approach can be used if the vessel tree is fairly complex with many narrow blood vessels, making it difficult to position a catheter without the help of the wire.

The guide catheter (or the second catheter in the alternative) is provided at the proximal end with an inlet for saline. Preferably a Luer® lock is provided so that a syringe can easily be connected to the catheter. The sensor unit is coupled to a control unit for the processing of the signals from the sensor unit, said signals being transferred via electrical leads running along the wire.

The method according to the invention will now be described in some detail with reference to the figures.

When the above-mentioned catheter has been positioned appropriately, it will become filled with blood because of the prevailing pressure difference between the interior of the body and the ambient atmosphere (i.e., the pressure inside the vessel is slightly higher than the atmospheric pressure externally of the body, $P_{body} - P_{outside} > 0$). When the wire carrying the sensor has been inserted and the sensor appropriately located at the point of measurement, the operator fills a syringe with a suitable amount of cold saline, say 20° C. The volume to be expelled by the syringe is preferably equal to the volume inside the catheter from the inlet point up to the outlet plus the bolus-dose to be expelled into the flowing blood. The volume of a catheter is commonly about 3 ml, and a suitable bolus-dose could be, for example, 1–3 ml, although the exact volumes will of course differ from case to case.

The sensor is connected via the electrical leads to a detection unit which has the capability of switching between measurement of cable resistance and detecting the signal from the sensor.

The operator connects the syringe to the inlet port and begins injecting the cold saline at a relatively low rate, such that the time to fill the guide catheter all the way up to the outlet will typically take 1–15, preferably 10–15 seconds, although this can vary substantially from case to case outside this interval. The volume of the catheter is known and thus when the operator has expelled a volume corresponding to the catheter volume during the mentioned time period, he will more rapidly expel the last dose, for example during 0.5 seconds, although this time is not strictly critical.

The detection unit operates according to the method disclosed in the previously mentioned U.S. provisional No. 60/136,401. The compensation disclosed therein is based on a switching between measurements of the sensor signal and of the resistance of the leads so as to enable compensation of changes in lead resistance. Thus, when the operator begins injecting the cold saline, the resistivity of the electrical leads will instantly be changed but this will be compensated for so that the detection unit will always deliver a readout of a constant temperature inside the blood vessel at the location of the sensor.

Figure 2A:
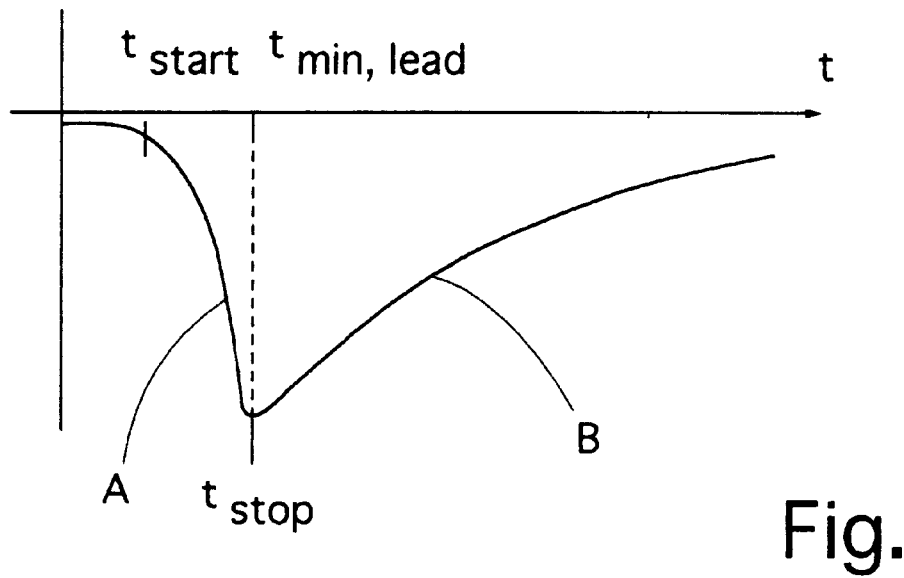
FIGS. 2a–d are graphs illustrating the resistivity profiles of the electrical leads during measurement.
Figure 2B:
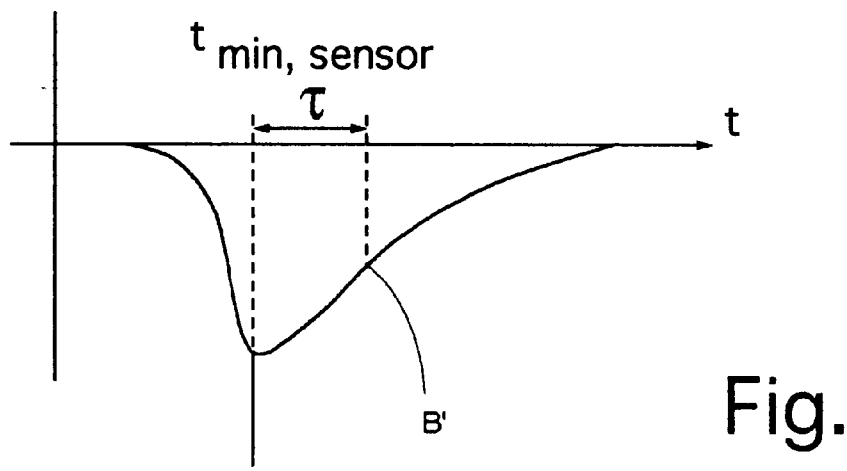

For the purpose of the invention, the change in resistance of the leads will not be recorded during the initial phase of filling the catheter with saline. But, immediately prior to or at the same time as the operator injects the last bolus-dose into the catheter, the recording of lead signal will be initiated and monitored and also the sensor signal will be recorded and monitored simultaneously. Because of the rapid injection of the last volume segment of cold saline (from the point $t_{start}$ in FIG. 2a to the point at which the bolus ends, $t_{stop}$), the cable resistivity will abruptly change since it will experience more cold liquid during a shorter period of time and this will be reflected in a drop in the readout signal as shown in FIG. 2a. The sensor being located at a relatively short distance from the catheter outlet, for example, approximately 10 cm (although this distance is not strictly critical), will be subjected to the cooler bolus-dose of saline a short period of time (on the order of a fraction of a second up to a few seconds) after it has been expelled from the outlet of the catheter. A sensor signal is schematically shown in FIG. 2b, and this signal is recorded and used as the basis for determining the starting point of time measurement.

Figure 2C:
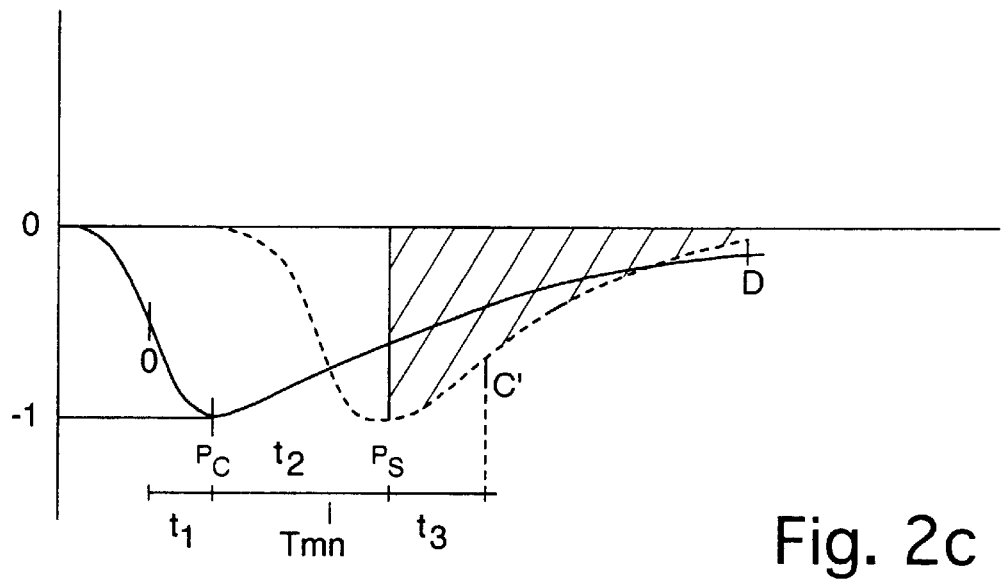
Figure 2D:
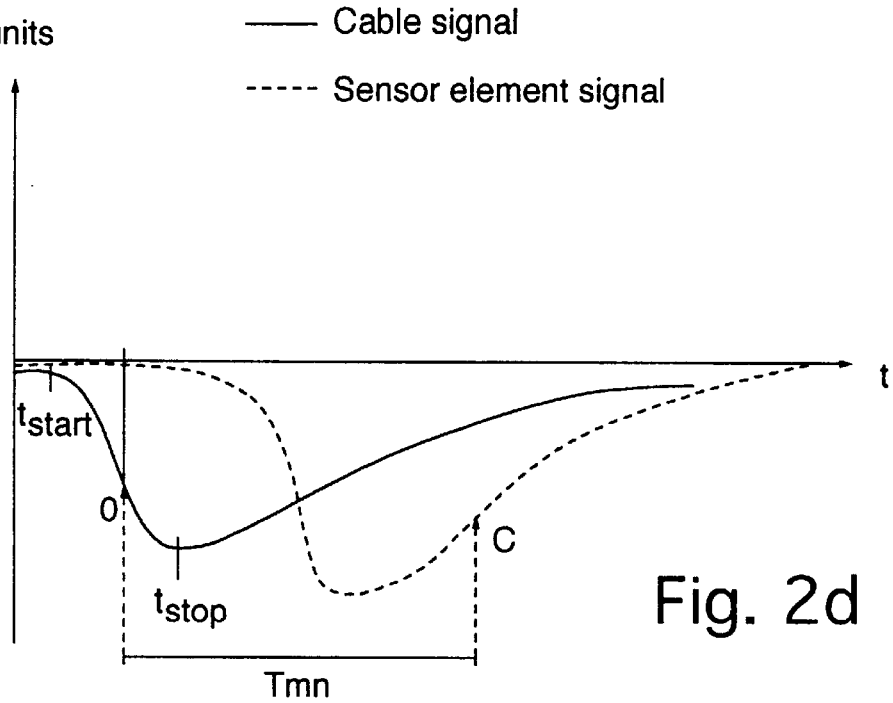

If it can be assumed that the actual injection of the bolus-dose into the blood-flow will not affect the measurement of the flow at the measurement point, then a calculation as recited under the background of the invention can be performed on the basis of the sensor signal by numeric integration, or by fitting the entire signal from the sensor element to a mathematical function (e.g., natural Log, Gamma), which can be used to calculate the center of mass of the curve defined by the sensor signal shown at C in FIG. 2(d). Also, a combination of numeric integration and curve fitting can be used. In the latter case, the curve fitting is performed at the portion of the curve approaching the base line, after the cut off point D (see FIG. 2c).

Figure 9:
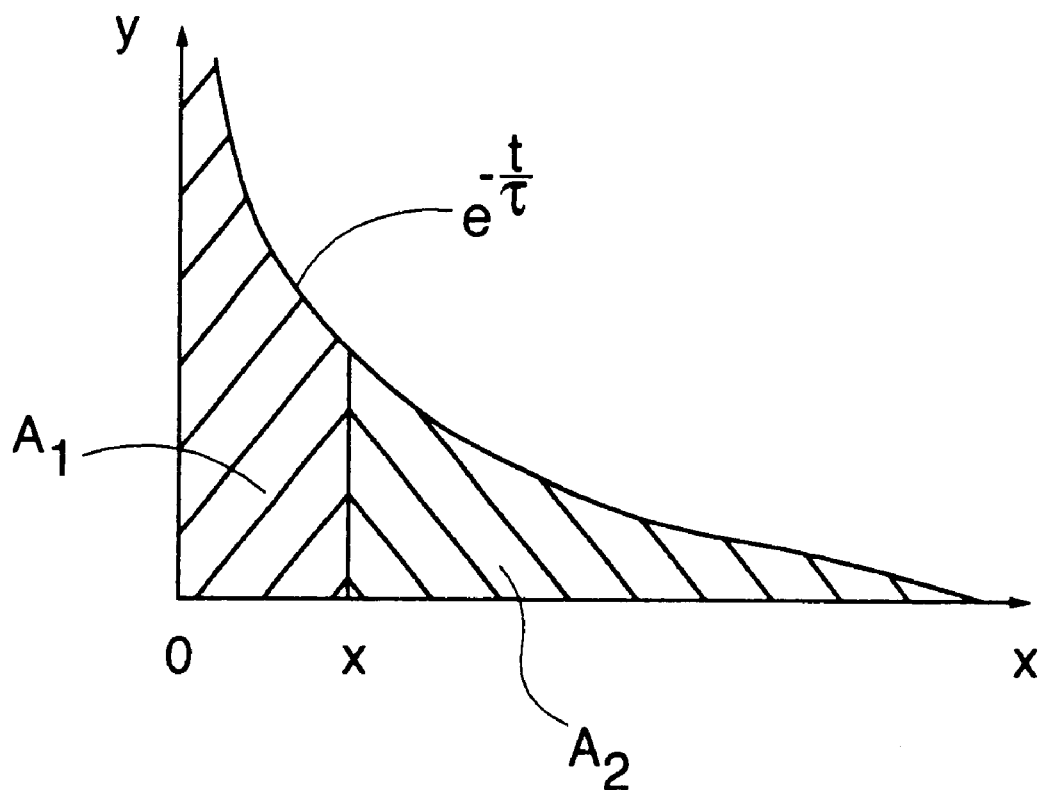
FIG. 9 illustrates a curve used in determining the center of mass.

To calculate the center of mass, we assume that it is located at a position x as shown in FIG. 9. The center of mass is found where the area of $A_1$=the area of $A_2$.

Accordingly, $$A_1 = \int_0^x e^{-t/\tau} dt \text{ and} \quad (3.12)$$

$$A_2 = \int_x^\infty e^{-t/\tau} dt \quad (3.13)$$

and, therefore:

$$A_1 = -\tau \, e^{-t/\tau} \Big|_0^x = -\tau \, e^{-x/\tau} + \tau \text{ and} \quad (3.14)$$

$$A_2 = -\tau \, e^{-t/\tau} \Big|_x^\infty = 0 + \tau \, e^{-x/\tau} \quad (3.15)$$

and, therefore, as $A_1 = A_2$, by substitution of equations 3.6a and 3.6b, it is known that $$-\tau e^{-x/\tau} + \tau = e^{-x/\tau}$$

it follows, therefore, that $2\tau e^{-x/\tau} = \tau$.

Dividing both sides of the equation by $\tau$ yields $2 e^{-x/\tau} = 1$ so that $e^{-x/\tau} = 0.5$.

Taking the natural logarithm of both sides yields: $-x/\tau = \ln(\frac{1}{2})$. It thus follows that:

$$x = -\tau \ln(\frac{1}{2}) = 0.7\tau \quad (3.16)$$

However, the starting point for the integration (i.e., t=0) must be determined. This point in time can be determined in different ways, using the recorded resistance variation curve. One way to determine t=0 to register the onset of resistivity reduction. Here the derivative of the curve may be calculated, and if the derivative exceeds a preset value, time measurement is triggered. Another way to determine t=0 is to use the peak value as a starting point for time measurement. Again the derivative, or preferably the second derivative, is calculated and the change in sign is detected. A further usable point is to take the average of the two values, e.g. $(t_{start} - t_{stop})/2$.

In an alternative embodiment the same "triggering" of the time measurement can be used. For the purposes of this invention, "triggering" is defined as the determination of a starting point for the time measurement, (i.e., the determination of t=0 for the purpose of integration).

In this alternative embodiment only the increasing part of the sensor signal (indicated with B' will be used). For this purpose the mentioned part B' (shown in FIG. 2b) of the sensor signal curve will entirely or partly be fitted to a mathematical function, e.g. $e^{-t/\tau}$, which is an exponential function. The simplest way of doing this is to take the logarithm of the measurement data along B' and to plot this against time. From the slope of the linear portion of that plot, the time constant, $\tau$ of the exponential function can be determined. The point on curve portion B' corresponding to the point on the time axis at $t_{min, sensor} + \tau$ will be center of mass of the exponential curve, which is the point up to which $T_{mn}$ will be calculated from t=0. As derived above, $0.7\tau$ should be used for the identification of the center of mass, but for the purpose of this invention the approximation to $\tau$ is adequate. $\tau$ can be calculated by fitting the sensor element signal from the point $P_s$ in FIG. 2c up to a point D, where D is the cut-off point, e.g. 10% of the peak value (at $P_s$).

If we assume that t=0 is equidistant from the points $t_{start}$ and $t_{stop}$, i.e., $(t_{stop} - t_{start})/2$, then the total mean transit time $T_{mn}$ will be sum $$T_{mn} = (t_{stop} - t_{start})/2 + t_{min, sensor} - t_{stop} + \tau \quad (3.17)$$

The terms of this sum are illustrated in FIG. 2c as $t_1$, $t_2$ and $t_3$ respectively, and thus $$T_{mn} = t_1 + t_2 + t_3 \quad (3.18)$$

wherein $\tau$ or $0.7\tau$ can be used for $t_3$, as indicated above.

Of the above possible approaches to the determination of $T_{mn}$, the method discussed in connection with FIG. 2d is the most in a mathematical accurate. However, the initial flank will very easily be affected by the injection, and the curve fitting may, therefore, be incorrect.

The other method (FIG. 2c), where only the portion after the peak is fitted to a curve is more independent of the injection, because the injection is stopped before any calculations are performed on the curve.

Figure 3:
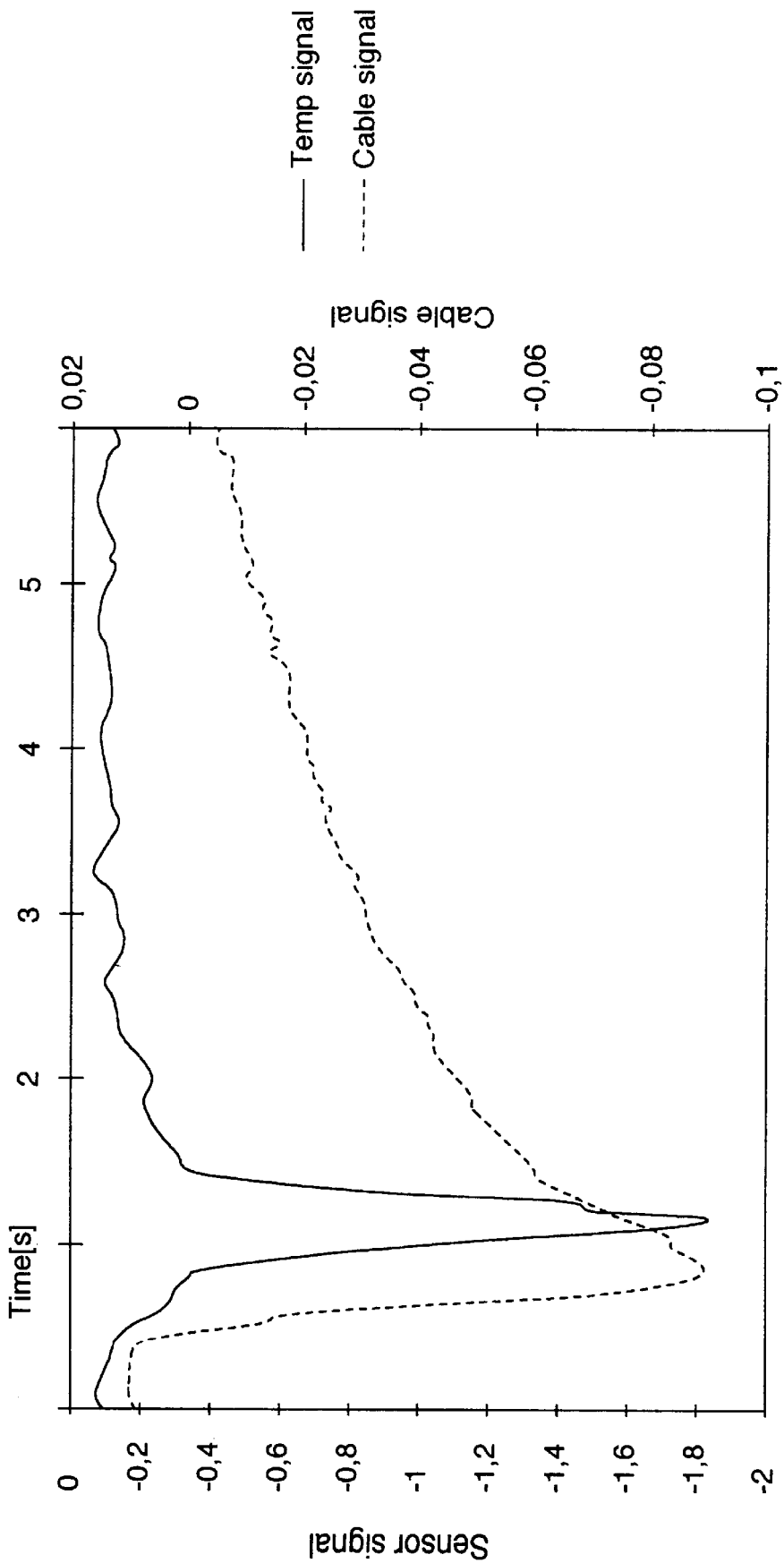
FIG. 3 is a graph showing measurements on a patient during hyperemia.
Figure 4:
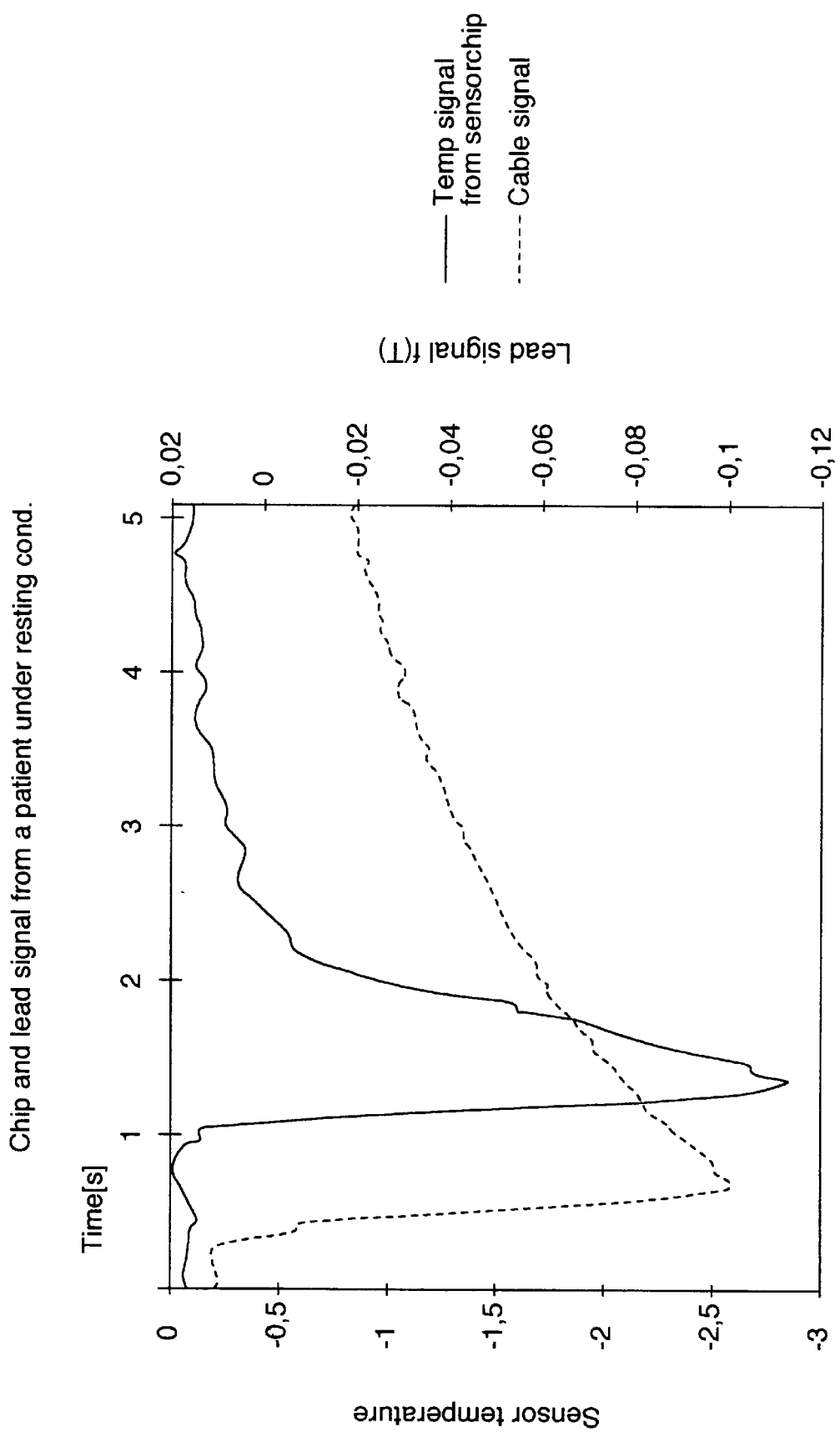
FIG. 4 is a graph showing measurements on a patient during a resting period.

In FIG. 3 and 4, respectively, measurement data on a patient are shown for a hyperemic condition and a resting condition respectively. As can be clearly seen in these figures there is a difference in the time between the minimum of the cable signal and the minimum of the temperature sensor response signal for the two cases. In the hyperemic state, the distance is shorter (i.e., the flow is higher) than in the resting condition. It is also clearly visible that the time constant for the increasing portion is slower for the resting condition than for the hypermia condition.

The CFR is calculated as $CFR = T_{mn, \, rest}/T_{mn, \, hyper}$ (3.19)

Figure 6:
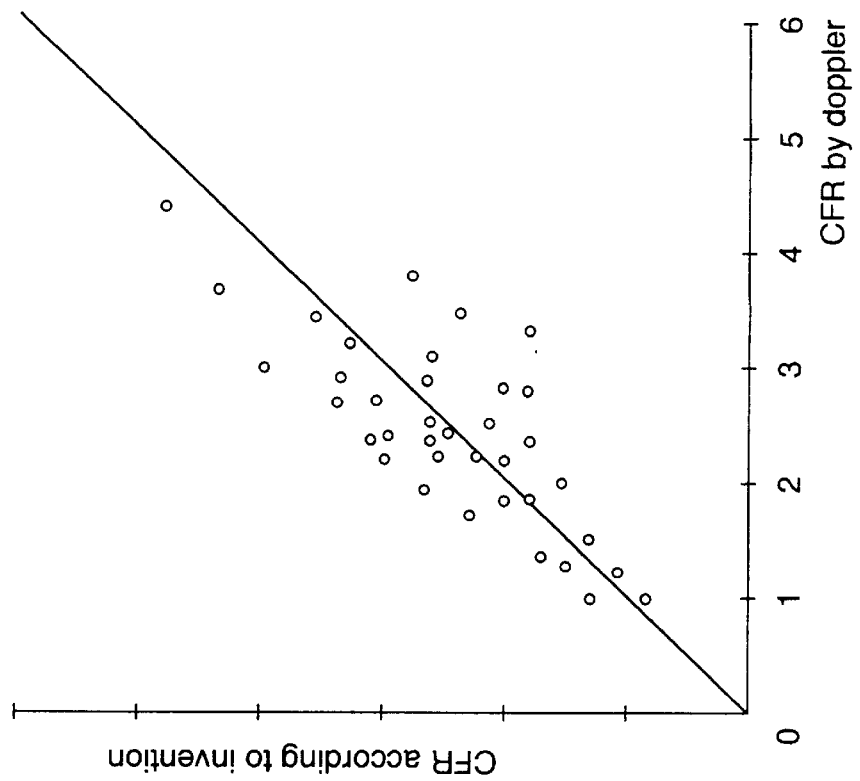
FIG. 6 is a graph showing the correlation between another set of patient data according to the invention and a reference method.
Figure 5:
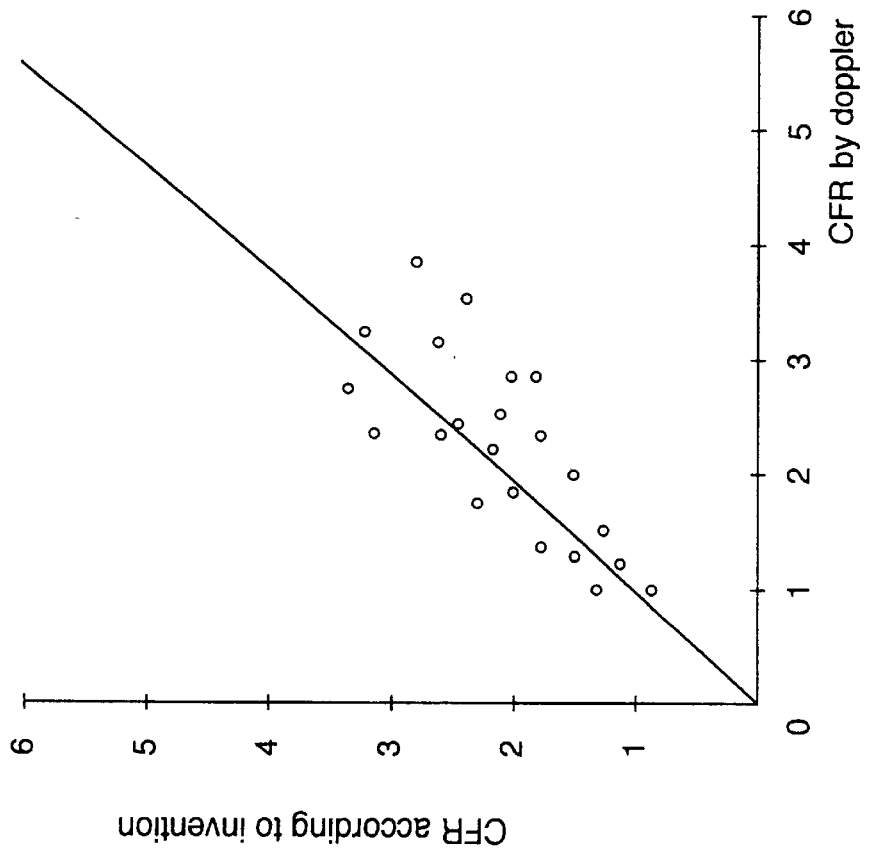
FIG. 5 is a graph showing the correlation between measurement data on patients according to the invention and a reference method.
Figure 7:
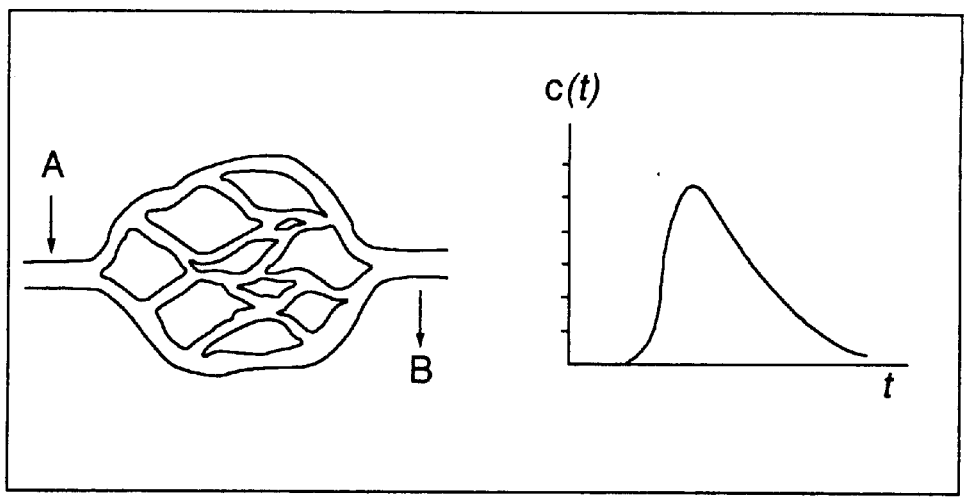
FIG. 7 illustrates an indicator dilution curve obtained in a vascular network.
Figure 8:
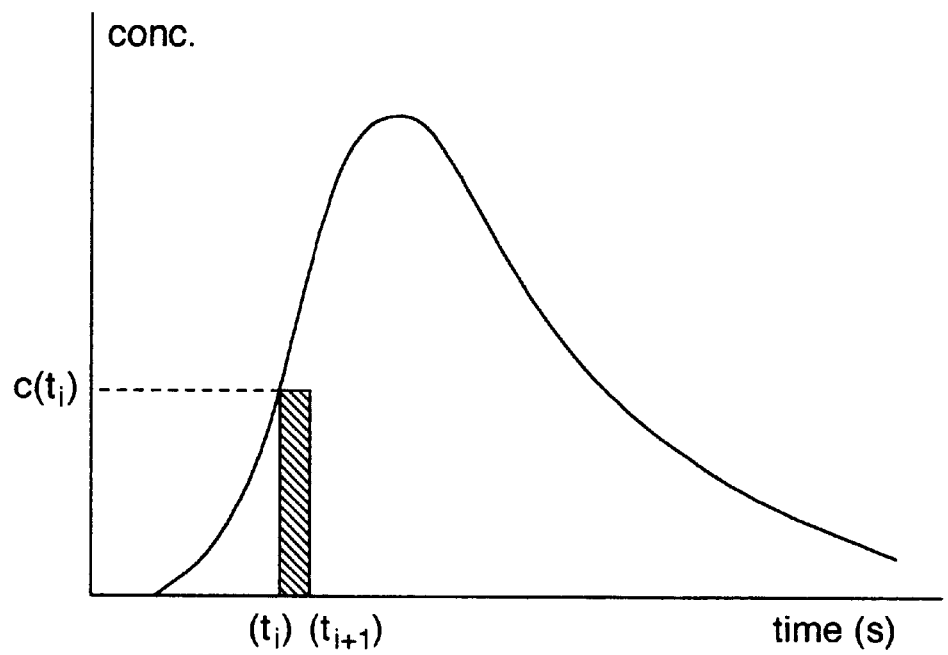
FIG. 8 illustrates calculation of flow in an indicator solution.

Finally in FIGS. 5 and 6, respectively, the method according to the invention has been qualitatively evaluated against a reference method which is a determination of CFR by a doppler-technique. In this case however, it should be noted that the doppler-technique also has its limitations and is not entirely accurate.

As previously disclosed in this application, CFR can be obtained by measuring the mean transit time, $T_{mn}$, for a bolus dose of cold liquid by employing the response curves from lead resistance measurements and a temperature sensor respectively.

For the calculation of $T_{mn}$, the time constant, $\tau$, of an exponential function $e^{-t/\tau}$ is calculated. It has also been discovered by the inventors that $\tau$ itself is correlated to the flow in a coronary vessel, and, therefore, $\tau$ itself can be used to determine a valve of CFR where $\tau_{rest}$ is the time constant of the temperature sensor response in a resting condition and $\tau_{hyper}$ is the time constant of the temperature sensor in a hyperemic condition. Accordingly, $CFR = \tau_{rest}/\tau_{hyper}$.

What is claimed is:

1. A method of triggering a time measurement in a system for the measurement of a transit time of a finite amount of an indicator first liquid injected in a flow of a second liquid in the course of a thermo-dilution measurement, wherein said flow of the second liquid has a different temperature than the temperature of said indicator first liquid, said system having a temperature sensitive part, said method of triggering comprising the steps of:

recording a change in electrical resistance caused by exposure of said temperature sensitive part of said system to said indicator first liquid; and using the recorded change to determine a starting point for time measurement.

2. The method as claimed in claim 1, wherein said temperature sensitive part of said system is at least one electrical lead connecting an electrical measuring device, located in said flow of said second liquid, with externally located control equipment.

3. The method as claimed in claim 2, wherein said electrical resistance is the electrical resistance of said at least one lead.

4. The method as claimed in claim 3, wherein a resistance variation of said electrical lead is registered, and wherein said method comprises the further steps of:
obtaining a resistance variation curve based on said resistance variation; and
selecting a point on said curve as said starting point for time measurement.

5. The method as claimed in claim 4, wherein said point is selected by calculating the derivative of said resistance variation curve, and taking a point in time where said derivative exceeds a predetermined level as said starting point.

6. The method as claimed in claim 4, wherein said point is selected by calculating the second derivative of said resistance variation curve, and taking a point in time where said second derivative changes sign as said starting point.

7. The method as claimed in claim 4, wherein said point is selected by calculating the average between the point in time when the injection of said indicator liquid is started and the point in time when the injection is stopped.

8. The method as claimed in claim 2, wherein said electrical measuring device is a temperature sensor.

9. The method as claimed in claim 1, wherein the temperature of said indicator liquid is lower than the second liquid, and wherein the second liquid is blood.

10. A method of determining a transit time of a finite amount of an indicator first liquid injected in a flow of a second liquid in the course of a thermo-dilution measurement, wherein said indicator first liquid has a temperature which is lower than the prevailing temperature inside a blood vessel, said method comprising the steps of:
providing a temperature sensor at the distal end of a wire;
providing electrical leads coupled to said sensor and running along the wire and connecting the leads to a control unit for the processing of signals from the sensor;
inserting a catheter having a distal end with an outlet and a proximal end with an inlet into the blood vessel so that the distal end is located in a region where a flow parameter is to be measured;
inserting the wire in said catheter and extending a distal end of the wire past the distal end of the catheter;
injecting said indicator first liquid into said catheter inlet so that the catheter is filled all the way up to the outlet;
injecting a further volume of said indicator first liquid to expel a corresponding volume of cold indicator first liquid into said blood vessel through the catheter outlet;
recording the resistance of the electrical leads and a response signal from the sensor;
determining a starting point for time measurements, t=0, from the resistance of the electrical leads;
determining a center of gravity of a sensor response curve;
calculating, as said flow parameter, a mean transit time $T_{mn}$ for the further volume of said indicator first liquid as the time from t=0 to the point in time corresponding to said center of gravity.

11. A method of determining a transit time of a finite amount of an indicator first liquid injected in a flow of a second liquid in the course of a thermo-dilution measurement, wherein said indicator first liquid has a temperature which is lower than the prevailing temperature inside a blood vessel, said method comprising the steps of:
providing a temperature sensor at a distal end of a wire;
providing electrical leads coupled to said sensor and running along the wire and connecting the leads to a control unit for the processing of signals from the sensor;
inserting the wire into the blood vessel so that the distal end is located in a region where a flow parameter is to be measured;
passing a catheter having a distal end with an outlet and a proximal end with an inlet over said wire to a point located proximally of the temperature sensor provided on said wire;
injecting said indicator first liquid into said catheter inlet so that the catheter is filled all the way up to the outlet;
injecting a further volume of said indicator first liquid to expel a corresponding volume of cold indicator first liquid into said blood vessel through the catheter outlet;
recording the resistance of the electrical leads and a response signal from the sensor;
determining a starting point for time measurements, t=0, from the resistance of the electrical leads;
determining a center of gravity of a sensor response curve;
calculating a mean transit time $T_{mn}$ for the further volume as the time from t=0 to the point in time corresponding to said center of gravity.

12. An apparatus for determining a transit time of a finite amount of an indicator first liquid injected in a flow of a second liquid in the course of a thermo-dilution measurement, said apparatus comprising:
a guide catheter having a proximal end and a distal end, wherein the guide catheter is adapted to be positioned in a blood vessel;
a syringe in fluid communication with the proximal end of said guide catheter, said syringe containing a quantity of said indicator first liquid;
a detection unit;
a wire positioned in said guide catheter, wherein a proximal end of the wire is adapted to be connected to the detection unit, and wherein a distal end of the wire is adapted to extend beyond the distal end of the guide catheter; and
a sensor attached to the distal end of the wire, wherein said sensor is adapted to monitor a variable and is adapted to produce a signal corresponding to the variable,
wherein the detection unit is adapted to switch between measuring the signal produced by the sensor and the resistivity of the wire, and wherein the detection unit uses the measurement of the resistivity of the wire to determine a starting point for the measurement of fluid flow.

13. The apparatus according to claim 12, wherein the sensor comprises a temperature sensor.

14. The apparatus according to claim 13, wherein the signal monitored by the sensor is the temperature of the second liquid.

15. The apparatus according to claim 13, wherein the sensor further comprises a pressure sensor.

16. The apparatus according to claim 12, wherein the syringe is connected to the guide catheter by a Luer lock.

17. The apparatus according to claim 12, wherein the indicator first liquid is saline.

* * * * *

UNITED STATES PATENT AND TRADEMARK OFFICE
CERTIFICATE OF CORRECTION

PATENT NO. : 6,672,172 B1 Page 1 of 1
DATED : January 6, 2004
INVENTOR(S) : Tulkki et al.

It is certified that error appears in the above-identified patent and that said Letters Patent is hereby corrected as shown below:

<u>Title page,</u>
Item [*] Notice, delete the phrase "by 166 days" and insert -- by 27 days --

Signed and Sealed this

Nineteenth Day of July, 2005

JON W. DUDAS
*Director of the United States Patent and Trademark Office*